United States Patent [19]

Dolle et al.

[11] Patent Number: 5,985,838
[45] Date of Patent: Nov. 16, 1999

[54] PEPTIDE ANALOGS AS IRREVERSIBLE INTERLEUKIN-1β PROTEASE INHIBITORS

[75] Inventors: Roland E. Dolle, King of Prussia; Irennegbe K. Osifo, W. Norrtion; Stanley J. Schmidt, Chester Springs; Denton W. Hoyer, Exton; Tina Morgan Ross, Anderson, all of Pa.; Prasad V. Chaturvedula, Cheshiye, Conn.; Catherine P. Prouty, Doylestown, Pa.; Mohamed M. A. Awad, Westerly, R.I.; Joseph M. Salvino, Schwenksville, Pa.; James M. Rinker, Hamdon, Conn.; Eric P. Lodge, Glendale, Ariz.; Jasbir Singh, Gilbertsville; Mark A. Ator, Paoli, both of Pa.

[73] Assignee: Vertex Pharmaceuticals, Inc., Cambridge, Mass.

[21] Appl. No.: 08/679,350

[22] Filed: Jul. 10, 1996

Related U.S. Application Data

[63] Continuation of application No. 08/371,723, Jan. 12, 1995, abandoned, which is a continuation-in-part of application No. 08/055,051, Apr. 29, 1993, abandoned.

[51] Int. Cl.$^6$ .................................................. A61K 38/05
[52] U.S. Cl. ................................ 514/19; 514/17; 514/18; 530/330; 530/331; 562/571
[58] Field of Search ..................... 514/17–19; 530/330, 530/331; 562/571

[56] References Cited

U.S. PATENT DOCUMENTS

| 5,055,451 | 10/1991 | Krantz et al. | 514/19 |
|---|---|---|---|
| 5,374,623 | 12/1994 | Zimmerman | 514/17 |
| 5,430,128 | 7/1995 | Chapman | 530/330 |

FOREIGN PATENT DOCUMENTS

| 0272671 | 12/1987 | European Pat. Off. . |
|---|---|---|
| 0519748 | 12/1992 | European Pat. Off. . |
| 9115577 | 10/1991 | WIPO . |
| WO-9115577 | 10/1991 | WIPO . |
| WO-9309135 | 5/1993 | WIPO . |

OTHER PUBLICATIONS

Dolle, R.E., et al. "P1 Aspartate–Based Peptide alpha–((2, 6–Dichlorobenzoyl) oxy) methyl Ketones as Potent Time Dependent Inhibitors of Interleukin–1beta–Converting Enzyme," *J. Med. Chem.* 37, pp. 563–564 (1994).

Thornberry, N.A., et al. "Inactivation of Interleukin–1beta Converting Enzyme by Peptide (Acyloxy)methyl Ketones," *Biochemistry* 33, pp. 3934–3940 (1994).

Sleath, P.R. et al. "Substrate Specificity of the Protease That Processes Human Interleukin–1beta," *J. Biol. Chem.* 24, pp. 14526–14528 (1990).

Thornberry, N.A., et al. "A Novel Heterodimeric Cysteine Protease is Required for Interleukin–1beta Processing in Monocytes," *Nature* 356, pp. 768–774 (1992).

Krantz, A., et al. "Peptidyl (Acyloxy) methyl Ketones and the Quiescent Affinity Label Concept: The Departing Group as a Variable Structural Element in the Design of Inactivators of Cysteine Proteinases," *Biochemistry* 30, pp. 4678–4687 (1991).

*Primary Examiner*—Cecilia J. Tsang
*Assistant Examiner*—David Lukton
*Attorney, Agent, or Firm*—Fish & Neave; James F. Haley, Jr. Esq.; Lisa A. Dixon

[57] ABSTRACT

Disclosed are compounds, compositions and methods for inhiβiting interleukin-1β protease activity, the compounds α-substituted methyl ketones having the formula (I) set forth herein. These compounds are inhibitors of IL-1β converting enzyme and as such are useful as therapeutic agents for certain infectious diseases.

11 Claims, No Drawings

PEPTIDE ANALOGS AS IRREVERSIBLE INTERLEUKIN-1β PROTEASE INHIBITORS

This application is a continuation of application Ser. No. 08/371,723 filed Jan. 12, 1995, now abandoned, which is a continuation-in-part of U.S. application Ser. No. 08/055,051, filed Apr. 29, 1993, now abandoned.

BACKGROUND OF THE INVENTION

1. Field of the Invention

This invention relates to peptide analogs that are interleukin-1β protease inhibitors. More particularly, the invention provides a-substituted methyl ketones derived from aspartic acid and the closed hemi-ketal forms thereof as inhibitors of interleukin 1-β protease.

2. Reported Developments

Enzymes involved in the catalytic degradation of proteins by hydrolyzing peptide bonds are known as proteases or proteinases. Proteinases are believed to be involved in various disease states including inflammation, metastasis, tissue damage, bone resorption and muscle degeneration in dystrophic diseases. Proteinases are divided into classes according to their catalytic mechanisms, such as serine-, cystein-, aspartic- and metallo-proteinases. For each class of proteinases, the catalytic site of the enzyme lies in the cleft on the surface of the enzymes in which reside the specificity subsites that bind amino acid side chains and the polypeptide backbone. In designing proteinase inhibitors, it is important to optimize the subsite binding characteristics with appropriate amino acid substrate analogs.

This invention relates to peptide substrates modified with affinity labels that inhibit interleukin-1β protease (hereinafter IL-1β protease). These inhibitors are thought to act by alkylating the cysteine sulfhydryl group (cys 285) within the catalytic site of IL-1β protease. Affinity labeling has been used since the 1960's to prepare irreversible peptide-based inhibitors which act to alkylate the active sites of cysteine proteases. A variety of affinity labels and amino acid sequences have been synthesized to improve the binding of these modified peptide inhibitors to the enzyme's active site. These affinity labels include peptidyl halomethyl ketones, peptidyl diazomethyl ketones, epoxysuccinyl peptides and peptidyl methylsulphonium salts as reviewed by D. Rich in Chapter 4 of "Proteinase Inhibitors", Barret, A. J. and Salvesen, G., eds., Elsevier, 1986. More recently, peptide acyloxymethyl and aryloxymethyl ketons have also been described as affinity lables (Krantz, A. et al, Biochemisty, 30, p. 4678–4687, 1991). Current research (see for example European Patent Application, Pub. No. 015,748 A2; PCT International Publication No. WO 91/15577; Chapman, K. T., Biorganic & Medicinal Chem. Lett. 1992, 2, 613–618) has been directed towards understanding the enzyme binding specificity requirements in designing novel small molecular weight protease inhibitors that are efficacious, safe and have specificity for IL-1β protease which is believed to play an important role in many disease states (see Epstein, F. H., New Engl. Jrl. of Med., 328, p. 106–113, 1993).

Disease states in which IL-1β protease inhibitors may be useful as therapeutic agents include: infectious diseases, such as meningitis and salpingitis; septic shock, respiratory diseases; inflammatory conditions, such as arthritis, cholangitis, colitis, encephalitis, endocerolits, hepatitis, pancreatitis and reperfusion injury, immune-based diseases, such as hypersensitivity, auto-immune diseases, such as multiple sclerosis; bone diseases; and certain tumors.

The following publications illustrate that IL-1β inhibitors and antagonists are useful in modifying certain disease states in vivo.

1) IL-1 is present in affected tissues in ulcerative colitis in humans. In animal models of the disease, IL-1β levels correlate with severity. In the model, administraton of IL-1ra reduced tissue necros and the number of inflammatory cells in the colon. Cominelli, F., Nast, C. C, Clark, B. D., Schindler, R., Llerena, R., Eysselein, V. E., Thompson, R. C., and Dinarello, C. A "Interleukin-1 gene expression, synthesis, and effect of cic IL-1 receptor blocke in rabbit immune complex colitis" J. Clin. Investigations (1990) Vol. 86, pp, 972–980.

2) IL-1ra supresses joint swelling in the PG-APS model of arthritis in rats. Schwab, J. H., Anderle, S. K., Brown, R. R., Dalldorf, F. G. and Thompson, R. C. "Pro- and Anti-Inflammatory Roles of Interelukin-1 in Recurrence of Bacterial Cell Wall-Induced Arthritis in Rats". Infect. Immun. (1991) 59; 4436–4442.

3) IL-1ra shows efficacy in an small open-label human RA trial. Lebsack, M. E., Paul, C. C., Bloedow, C. C., Burch, F. X., Sack, M. A., Chase, W., and Catalano, M. A. "Subcutaneous IL-1 Receptor Antagonist in Patients with Rheumatoid Arthritis" Arth. Rheum. (1991) 34; 545.

4) IL-1 appears to be an autocrine growth factor for the proliferation of CML cells. Both IL-1ra and sIL-1R inhibit colony growth in cells removed from leukemia patients. Estrov, Z., Kurzrock, R., Wetzler, M., Kantarjian, H., Blake, M., Harris, D., Gutterman, J. U., and Talpaz, M. "Supression of chronic myelogenous leukemia colony growth by interleukin-1 (IL-1) receptor antagonist and soluble IL-1 receptors: a novel application for inhibitors of IL-1 activity". Blood (1991) 78; 1476–1484.

5) As in 4) above, but for acute myclogenous leukemia rather than chronic myelogenous leukemia. Estrov, Z., Kurzrock, R., Estey, E., Wetzler, M., Ferrajoli, A., Harris, D., Blake, M. Guttermann, J. U., and Talpaz, M. "Inhibition of acute myelogenous leukemia blast proliferation by interleuldn-1 (IL-1) receptor antagonist and soluble IL-1 receptors". (1992) Blood 72, 1938–1945.

It is an object of the present invention to provide novel peptidyl substrate analogs modified with electronegative leaving groups that bind at the active site of IL-1β protease and inhibit IL-1β protease activity. IL-1β protease cleaves a biologically inactive 34 kD precursor of IL-1β to form the biologically active 17 kD cytokine. This cleavage occurs at the peptidyl sequence of Val-His-Asp/-Ala-Pro-Val.

It is another object of the present invention to provide compositions comprising the above-referred to compounds.

It is a further object of the present invention to provide a method of use of the composition for the treatment of the above-identified disease states.

SUMMARY OF THE INVENTION

According to the present invention, there is provided a compound of the formula (I) and a pharmaceutically acceptable salt thereof:

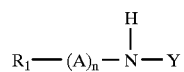

Formula I wherein $n=0-4$;

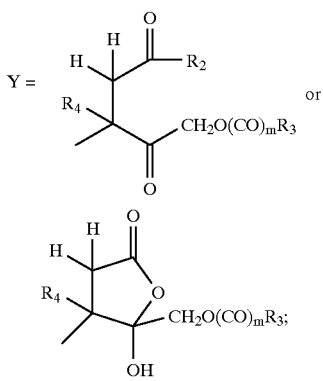

$m=0,1$;

$R_3$ = a singularly or multiply substituted aryl wherein aryl is a phenyl or naphthyl ring wherein the substituents are independently selected from the group consisting of:
(1) H
(2) halogen
(3) OH
(4) $CF_3$
(5) $NO_2$
(6) $OR_5$
(7) $COR_9$
(8) $NR_6COR_{10}$
(9) $CONR_5R_6$
(10) $SO_2NR_5R_6$
(11) $SO_2R_6$
(12) $COOR_{11}$

(13) 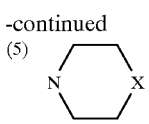 —O—$(CH_2)_{1-6}$— ⌬ —$OR_{11}$ and
(14) lower alkyl and lower cycloalkyl;

$R_5$ =
(1) lower straight chain or branched alkyl, lower cycloalkyl
(2) $(CR_6R_7)_{0-6}$-aryl
(3) $(CR_6R_7)_{0-6}$-heteroaryl or
(4) $(CR_6R_7)_{2-6}$-$R_8$;

$R_6$ and $R_7$ are independently H, lower straight chain or branched alkyl, benzyl, aryl, cycloalkyl and aryl is defined as above and heteroaryl includes pyridyl, thienyl, furyl, thiazolyl, imidazolyl, pyrazolyl, isoxazolyl, benzimidazolyl, pyrazinyl, pyrimidyl, quinolyl, isoquinolyl, isothiazolyl, benzofuranyl, isoxazolyl, triazinyl and tetrazolyl;

$R_8$ =
(1) $OCH_2CH_2OR_6$
(2) $OCH_2CH_2NR_6R_7$
(3) $NR_6CH_2CO_2R_6$ (4) 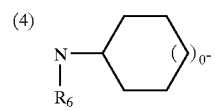

(5) 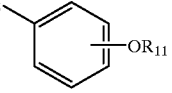

X=O,S and
(6) $NR_6R_7$ wherein $R_6$ and $R_7$ are as above defined;

$R_9$ =
(1) lower straight chain or branched alkyl, lower cycloalkyl
(2) $(CR_6R_7)_{0-6}$-aryl;
(3) $(CR_6R_7)_{0-6}$-heteroaryl; or
(4) $(CR_6R_7)_{0-6}$-$R_8$, wherein $R_6$, $R_7$ and $R_8$ are as above defined;

$R_{10}$ =
(1) $R_9$
(2) $OR_{11}$
(3) $NR_6R_{11}$, wherein $R_{11}$ =
(1) lower straight chain or branched alkyl, lower cycloalkyl
(2) $(CR_6R_7)_{1-6}$-aryl;
(3) $(CR_6R_7)_{1-6}$-heteroaryl; or
(4) $(CR_6R_7)_{2-6}$-$R_8$, and $R_6$, $R_7$ and $R_8$ are as above defined;

$R_4$ = H or deuterium;

$R_2$ =
(1) $OR_6$
(2) $NR_6OR_7$ or
(3) $NR_6R_7$, and $R_6$ and $R_7$ are as above-defined;

A=
(1) an amino acid of the formula (II)

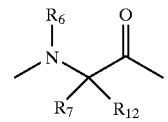

Formula 2 wherein $R_6$ and $R_7$ are as defined above;

$R_{12}$ is independently
(1) H or
(2) $(CR_6R_7)_{1-6}$-$R_{13}$, and $R_6$ and $R_7$ are as above-defined;

$R_{13}$ =
(1) H
(2) F
(3) $CF_3$
(4) OH
(5) $OR_{11}$
(6) $NR_6R_{14}$
(7) cycloalkyl
(8) aryl
(9) heteroaryl
(10) SH
(11) $SR_{11}$
(12) $CONR_5R_6$

(13) COOR$_5$ or

(14) [structure: phenyl with —OR$_{11}$]

R$_{14}$=
(1) R$_7$
(2) COR$_{10}$
(3) SO$_2$NR$_5$R$_6$ or (4) [structure: CH$_3$—C(=NR$_6$)—NR$_6$R$_7$]

or

A=
(2) an amino acid selected from the group consisting of (1) [N-methyl aziridine-2-acetyl structure]

(2) [N-methyl pyrrolidine-2-acetyl structure]

(3) [1-methyl indoline-2-acetyl structure]

(4) [octahydro-1-methyl-indole-2-acetyl structure]

(5) [N-methyl isoindoline-1-acetyl structure]

(6) [octahydro-isoindole-1-acetyl structure]

(7) [N-methyl piperidine-2-acetyl structure]

(8) [N-methyl tetrahydroisoquinoline-3-acetyl structure]

(9) [decahydro-N-methyl isoquinoline-3-acetyl structure]

(10) [N-methyl tetrahydroquinoline-2-acetyl structure] and

(11) [decahydro-N-methyl quinoline-2-acetyl structure]

(12) [N-methyl azepane-2-acetyl structure]

R$_1$ is an acyl group of the formula (III)

Formula III

[structure: R$_{12}$—C(=O)—]

wherein
R$_{12}$ is
(1) OR$_5$
(2) NR$_5$R$_6$
(3) R$_5$
(4) —CH=CHR$_5$ (5) [phenyl with R$_5$O— substituent]

(6) R$_5$R$_6$N—(CH$_2$)$_{1-4}$—[phenyl]

-continued (7) 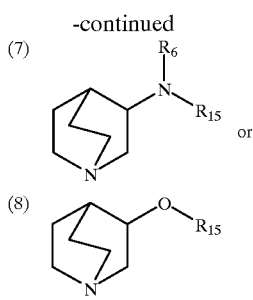

or (8) 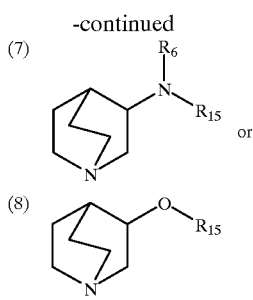

wherein
$R_{15}$=single bond, $(CH_2)_{2-6}$-$NR_6$—, $(CH_2)_{2-6}$O— and $R_5$ and $R_6$ are as above defined; or
a sulfonyl group of the formula (IV)

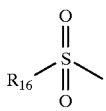

Formula IV wherein
$R_{16}$ is
(1) $R_5$ (2) 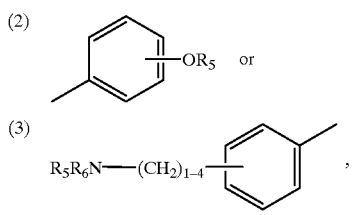

or (3) 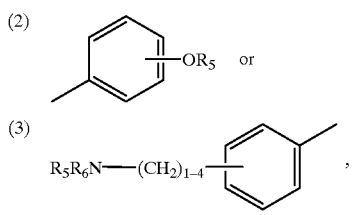

wherein $R_5$ and $R_6$ are as above-defined.

As used herein the term pharmaceutically acceptable salts include the acid and base addition salts.

The term acid addition salts refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid,citric acid, benzoic acid, cinnamic acid, mandelic acid, methanesulfonic acid, ethanesulfonic acid, p-toluenesulfonic acid, salicylic acid and the like.

The term base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

"Alkyl" means a saturated or unsaturated aliphatic hydrocarbon which may be either straight- or branched-chain. Preferred groups have no more than about 12 carbon atoms and may be methyl, ethyl and structural isomers of propyl, butyl, pentyl hexyl heptyl, octyl, nonyl, decyl undecyl and dodecyl.

"Lower alkyl" means an alkyl group as above, having 1 to 7 carbon atoms. Suitable lower alkyl groups are methyl ethyl, n-propyl isopropyl butyl tert-butyl, n-pentyl, neopentyl, n-hexyl, and n-heptyl.

"Substituted phenyl" means a phenyl group in which one or more of the hydrogens has been replaced by the the same or different substituents including halo, lower alkyl, nitro, amino, acylamino, hydroxyl, lower alkoxy, aryl, heteroaryl, lower alkoxy, alkylsulfonyl, trifluoromethyl, morpholinoethoxy, morpholino-sulfonyl, and carbobenzoxy-methyl sulfamoyl.

"Halogen" means chloride, fluoride, bromide or iodide.

"Lower cycloalkyl" means cycloalkyl having $C_3$ to $C_6$ carbon atoms.

The present invention also concerns the pharmaceutical composition and method of treatment of IL-1β mediated disease states or disorders in a mammal in need of such treatment comprising the administration of IL-1β inhibitors of formula (I) as the active agent These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseass, such as hypersensitivity; auto-immune diseases, such as multiple sclerosis; bone diseases; and certain tumors.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectally, buccally (including sublingually), transdermally or intranasally. The most suitable route in any given case will depend upon the use, the particular active ingredient, and the subject involved. The compound or composition may also be administered by means of controlled-release, depot implant or injectable formulations as described more filly herein.

In general, for the uses as described in the instant invention, it is expedient to administer the active ingredient in amounts between about 0.1 and 100 mg/kg body weight, most preferably form about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to 10 mg/kg of body weight.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

A further aspect of the present invention relates to pharmaceutical compositions comprising as an active ingredient a compound of the present invention in admixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, syrup, methylcellulose, polyoxyethylene sorbitar monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences*, 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, desoxycholic acid, chenodesoxycholic acid, dehydrocholic acid, glycodeoxy-cholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

DETAILED DESCRIPTION OF THE INVENTION

Compounds of the present invnetion are prepared using the procedure described generally in Schemes I, II and III and in more detail described in the Examples.

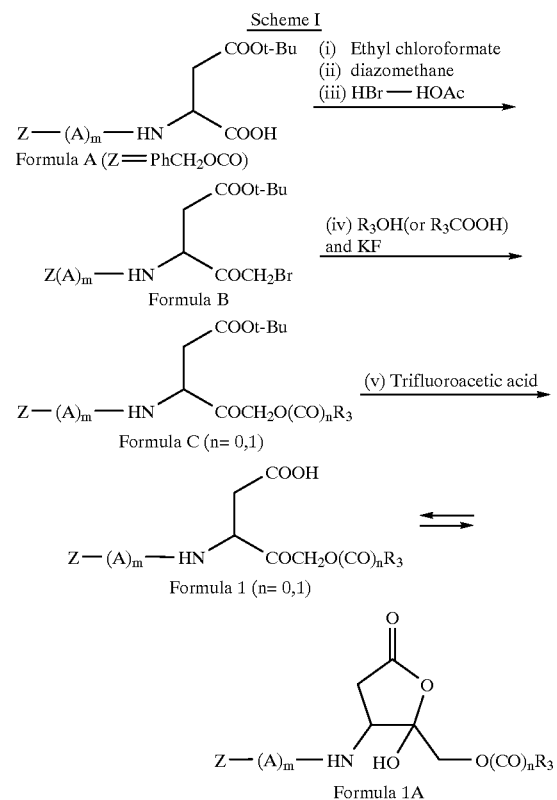

wherein A, $R_3$ and m are as defined in formula (I) and Z is benzyloxycarbonyl.

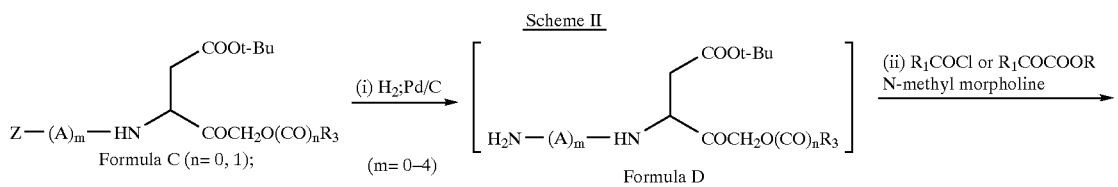

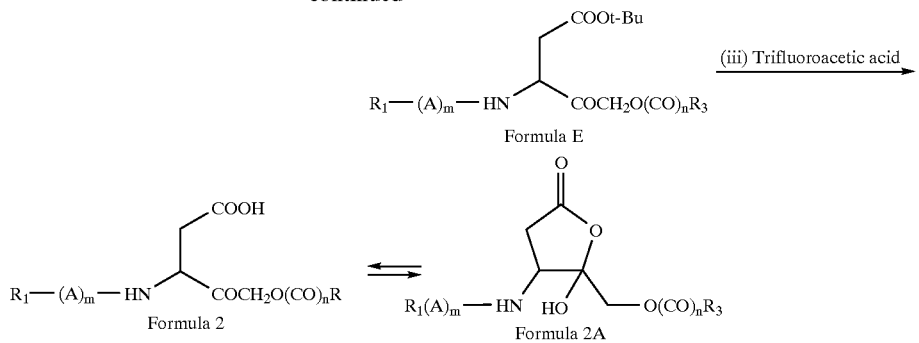

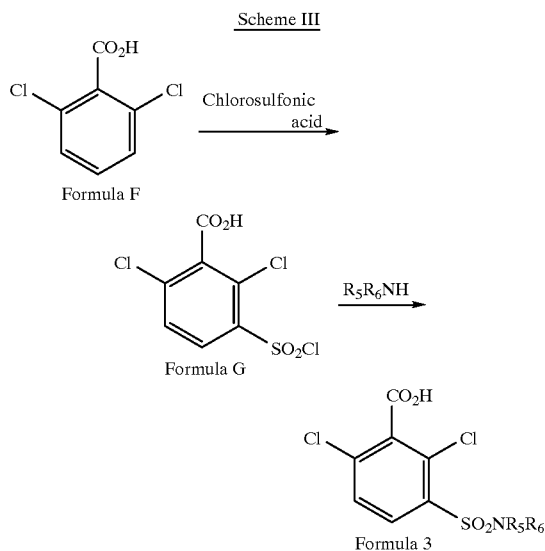

wherein Z, A, $R_1$, $R_3$, m and n are as defined in formula (I).

Methods of Preparation

The synthesis of the disclosed interleukin enzyme (ICE) inhibitors was conducted by one of two methods depicted in Schemes I and II. For inhibitors which contained an N-terminal benzyloxycarbonyl group ("Z" group), N-benzyloxycarbonyl-L-aspartic acid mon t-butyl ester or other benzyloxycarbonyl protected aspartic acid-based peptides (Formula A) were used as starting materials. The synthesis of the requisite peptides are readily carried out by a variety of methods known to those practicing in the art of peptide chemistry. The aspartic acid-based peptide (Formula A) is reacted with ethyl chloroformate and N-methyl morpholine in tetrahydrofuran (THF) at low temperature (ca −15° C.) for approximately 30 min. This generates a mixed anhydride in solution thereby activating the free carboxylate toward nucleophilic attack. Other activating reagents (e.g. isopropyl chloroformnate), solvents (diethyl ether, dioxane), and tertiary amine bases (diisopropyl ethyl amine, triethyl amine) can be used in place of the above preferred reagents to form a reactive carboxylate species. The pre-formed mixed anhydride is treated (without isolation) with a solution of diazomethane in diethyl ether. The diazomethane reagent is prepared under standard conditions from DIAZALD® using a commercially available (Aldrich) diazomethane generator. A one to two molar excess of diazomethane is added and the reaction mixture is warmed from −15° C. to 25° C. over a 20 min period. During this time, diazomethane reacts with the mixed anhydride to form an a-diazoketone. The a-diazoketone is not isolated by the action mixture is treated directly with an excess of a 1:1 solution of 48% hydrobromic (HBr) and glacial acetic (HOAc) acids. The mixture of acids are added dropwise to the a-diazoketone and the reaction mixture is subsequently stirred for at least 15 minutes. This treatment with 1:1 48% HBr and glacial HOAc decomposes the a-diazoketone to yield the desired N-benzyloxrbonyl-L-aspartic acid mono t-butyl ester a-bromoketone (Formula B) and nitrogen gas as a by-product. The bromomethyl ketone is typically isolated as an oil using standard procedures which are apparent to those skilled in the art. The a-bromoketone so obtained is of sufficient purity to be used in all subsequent reactions. However, the, ketone can be further purified by high pressure liquid chromatography (HPLC), if analytically pure material is desired.

The t-butyl ester a-bromoketone (Formula B) is subsequently reacted with a variety of phenols, naphthols, and arylcarboxylic acids. This is conducted by exposing the bromomethyl ketone to an excess of the phenol or arylcarboxylic acid in dimethylformamide containing sodium or potassium hydride or potassium fluoride. The reaction can be conveniently monitored by thin layer chromatography (TLC) and once the TLC indicates that displacement of the bromide with the phenol or carboxylate is completed, the product is isolated using standard procedures. The desired aspartic acid mono t-butyl ester a-aryloxymethyl- or a-arylacyloxymethyl ketone (Formula C) may be purified by conventional methods including recrystallization and silica gel column chromatography.

The remaining synthetic transformation to generate the ICE inhibitors is the hydrolysis of the t-butyl ester function. This is conducted by exposing the t-butyl ester (Formula C) to a 25% solution of trifluoroacetic acid (TFA) in methylene chloride at 25° C. The de-esterification is typically complete within 3 hrs. Removal of the volatile TFA and organic solvent affords the aspartic acid (Formula 1). The yield of the reaction is quantitative in most instances, providing the t-butyl ester starting material is of high purity. Purification, if required, can be performed by recrystallization or chromatographic techniques which are well known to those skilled in the art The concentration of TFA may range from 5%–100% and other organic solvents may be used such as chloroform. Alternatively, a solution of three molar anhydrous hydrochloric acid in ethyl acetate may be used in place of the TFA-methylene chloride solution with equal efficiency. the $^1$H NMR spectra of these acids of Formula 1 indicate that they exist in equilibrium as the closed hemiketal form shown in Formula 1A and that the ratio of Formula 1 versus Formula 1A is solvent dependent.

In Scheme II, the synthesis of aryloxy- and arylacyloxymethyl ketones (Formula 2) which possess an N-terminal group other than the Z-group are described. The aspartic acid derivatives of Formula C are the stating material for the synthesis of inhibitors of Formula 2. First the Z-group is removed to generate the N-terminal amine (Formula D) under hydrogenolytic conditions. The reagents and conditions typically used to carry out the hydrogenolytic removal of the Z-group are hydrogen gas, ambient temperature conditions and pressure, 5% palladium on carbon as the catalyst in an alcoholic solvent e.g., methanol optionally containing two equivalents of hydrochloric acid. It is not necessary to purify the intermediate free amine (or the hydrochloride salt if hydrochloric acid is used in the hydrogenolysis), though this material needs to be dry and free of alcohol for the subsequent coupling reaction to proceed in good yield.

The N-terminal amine is then condensed with a carboxylic acid to yield intermediates of Formula E. It is generally necessary to first activate the acid as an acid chloride or mixed anhydride and then react it with the free amine (or hydrolchloride salt) in the presence of an organic base, e.g., N-methylmorpholine. Alternatively, coupling with acid with the intermediate amine is conducted using amide coupling reagents/conditions employed in peptide coupling chemistry ("The Practice of Peptide Synthesis", M. Bodanszky, Springer-Verlag, New York, 1984; "The Peptides", Vol 1–3, E. Gross and J. Meienhofer, Eds. Academic Press, New York, 1981). Lastly, the t-butyl ester in Formula E is removed with trifluoroacetic acid (as described above) to give the aspartic acid analogs of Formula 2. As in the case of the compounds of Formula 1, the $^1$H NMR of components of Formula 2 appear to exist in equilibrium with their corresponding closed hemiketal counterparts of Formula 2A.

The phenols, naphthyls and arylcarboxylic acids used in the reaction with the bromomethyl ketones can be either purchased form commercial sources or synthesized by adopting known procedures. Their synthesis would be readily deduced by those skilled in the art of organic synthesis. By way of example, the preparation of the 2,6-dichloro-3-sulfonamido benzoic acids are presented in Scheme III. Thus, 2,6-dichlorobenzoic acid (Formula F; available from Aldrich Chemical Co.) is reacted with chlorosulfonic acid to yield the intermediate sulfonyl chloride (Formula G). The electrophilic sulfonyl chloride is reacted with a variety of amines to give the substituted benzoic acids (Formula 3).

Intermediate compounds for use in making the final compounds of the present invention are described in Examples 1–37.

EXAMPLE 1

N-Benzyloxycarbonyl-L-aspartic acid bromomethyl ketone b-tert-butyl ester

To a solution of N-benzyloxycarbonyl L-aspartate b-tert-butyl ester (Formula A; 10 g, 31 mmol) in 70 ml of anhydrous THF at –15° C. was added N-methyl morpholine (4.7 ml, 43.4 mmol) followed by the dropwise addition of ethyl chloroformate (3.9 ml, 40.5 mmol). The reaction mixture was stirred for 30 min at –15° C. and the suspension treated with diazomethane in ether (160 ml of a 0.4 in solution in ether, prepared from "DIAZALD®" [Aldrich]) and warmed to room temperature.

The bromomethyl ketone was formed in the same pot by cooling the intermediate diazoketone above followed by the dropwise addition of a 1:1 solution of 48% hydrobromic acid and glacial acetic acid (62 ml). After stirring for 15 min the reaction mixture was poured into a separatory funnel. The aqueous layer was drawn off and discarded. The remaining organic phase was washed with water, saturated aqueous NaHCO$_3$, brine and dried (MgSO$_4$). The solvents were removed in vacuo and the title compound so obtained (m.p. 41–43° C.) was used in the subsequent displacement reactions without further purification.

EXAMPLE 2

N-Benzyloxycarbonyl-L-Aspartic Acid 2,6-dichlorobenzoyloxymethyl Ketone b-tert-Butyl Ester N-Benzyloxycarbonyl-L-aspartic acid bromomethyl ketone b-tert-butyl ester (0.30 g; 0.76 mM) was dissolved in 12 ml of anhydrous DMF. To this solution was added powdered potassium fluoride (0.11 g; 19 mmol) and 2,6-dichlorobenzoic acid (0.17 g; 0.91 mmol) and the reaction mixture was stirred overnight The solution was diluted with Et$_2$O and washed with water, aqueous saturated NaHCO$_3$, brine and dried (MgSO$_4$). The ketone so obtained was purified by silica gel chromatography using ethyl acetate/hexane as the eluting solvent ($^1$H NMR (CDCl$_3$) d 7.35 (m, 8H)), 5.90 (d, 2H each), 5.20 (m, 4H), 4.70 (m, 1H), 3.00 and 2.75 (doublet of doublets, 1H each), 1.42 (m, 9H).

In a similar manner, the following compounds of formula B were prepared:

EXAMPLE 3

N-Benzyloxycarbonyl-L-aspartic acid 2,6-difluorophenoxymethyl ketone β-tert-butyl ester from N-benzyloxycarbonyl-L-aspartic acid bromomethyl ketone β-tert-butyl ester and 2,6-difluorophenol (mp 50–51° C.).

EXAMPLE 4

N-Benzyloxycarbonyl-L-aspartic acid 2,6-ditrifluoromethyl benzyloxymethyl ketone β-tert-butyl ester from N-benzyloxycarbonyl-L-aspartic acid bromomethyl ketone β-tert-butyl ester and 2,6-ditrifluoromethyl benzoic acid (mp 62–63° C.).

EXAMPLE 5

N-Benzyloxycarbonyl-L-aspartic acid 2,6-dichlorophenoxymethyl ketone β-tert-butyl ester from N-benzyloxycarbonyl-L-aspartic acid bromomethyl ketone β-tert-butyl ester and 2,6-dichloro-phenol.

EXAMPLE 6

N-Benzyloxycarbonyl-L-aspartic acid 2-fluoro-(N-morpholinyl sulfonamido)phenoxymethyl ketone β-tert-butyl ester from N-benzyloxycarbonyl-L-aspartic acid bromomethyl ketone β-tert-butyl ester and 2-fluoro-4-(N-morpholinylsulfonamido)phenol.

EXAMPLE 7

N-Benzyloxycarbonyl-L-aspartic acid 2-chloro-4-(N-thiomorpholinylsulfonamido)phenoxymethyl ketone β-tert-butyl ester from N-benzyloxycarbonyl-L-aspartic acid bromomethyl ketone β-tert-butyl ester and 2-chloro-4-(N-thiomorpholinyl sulfonamido)phenol.

EXAMPLE 8

N-Benzyloxycarbonyl-L-aspartic acid 2,6-dichloro-3-(2-N-morpholinylethoxy)benzoyloxymethyl ketone β-tert-butyl ester from N-benzyloxycarbonyl-L-aspartic acid bromom-

EXAMPLE 9
N-Benyloxycarbonyl-L-aspartic acid 2,6dimethoxy benzoyloxymethyl ketone β-tert-butyl ester from N-benzyloxycarbonyl-L-aspartic acid bromomethyl ketone β-tert-butyl ester and 2,6-dimethoxy-benzoic acid.

EXAMPLE 10
N-Benzyloxycarbonyl-L-aspartic acid 2,6-dichloro-3-(benzyloxy) benzoyloxymethyl ketone β-tert-butyl ester from N-benzyloxycarbonyl-L-aspartic acid bromomethyl ketone β-tert-butyl ester and 2,6-dichloro-3-(benzyloxy) benzoic acid.

EXAMPLE 11
N-Benzyloxycarbonyl-L-aspartic acid 2-acetamido-6-chloro benzoyloxymethyl ketone β-tert-butyl ester from N-benzyloxycarbonyl-L-aspartic acid bromomethyl ketone β-tert-butyl ester and 2-acetamido-6-chlorobenzoic acid.

EXAMPLE 12
N-Benzyloxycarbonyl-L-aspartic acid 2,6-difluorobenzoyloxy-methyl ketone β-tert-butyl ester from N-benzyloxycarbonyl-L-aspartic acid bromomethyl ketone β-tert-butyl ester and 2,6-difluorobenzoic acid.

EXAMPLE 13
N-Benzyloxycarbonyl-L-aspartic acid 3-(N-butylsulfonamido)-2,6-dichlorobenzoyloxymethyl ketone β-tert-butyl ester from N-benzyloxycarbonyl-L-aspartic acid bromomethyl ketone β-tert-butyl ester and 3-(N-butylsulfonamido)-2,6-dichlorobenzoic acid.

EXAMPLE 14
N-Benzyloxycarbonyl-L-aspartic acid 2,6-dichloro-3-sulfonamido benzoyloxymethyl ketone β-tert-butyl ester from N-benzyloxycarbonyl-L-aspartic acid bromomethyl ketone β-tert-butyl ester and 2,6-dichloro-3-sulfonamidobenzoic acid.

EXAMPLE 15
N-Benzyloxycarbonyl-L-aspartic acid-3-(N-benzylsulfonamido)-2,6-dichlorobenzoyloxymethyl ketone β-tert-butyl ester from N-benzyloxycarbonyl-L-aspartic acid bromomethyl ketone β-tert-butyl ester and 3-(N-benzylsulfonamido)benzoic acid.

EXAMPLE 16
N-Benzyloxycarbonyl-L-aspartic acid 3-(N-[2-aminoacetamidoyl] sulfonamido)-2,6-dichlorobenzoyloxymethyl ketone β-tert-butyl ester from N-benzyloxycarbonyl-L-aspartic acid bromomethyl ketone β-tert-butyl ester and 3-(N-[2-aminoacetamidoyl] sulfonamido)-2,6-dichlorobenzoic acid.

EXAMPLE 17
N-Benzyloxycarbonyl-L-aspartic acid 2,6-dichloro-3-(N-morpholinylsulfonamido)benzoyloxymethyl ketone β-tert-butyl ester from N-benzyloxycarbonyl-L-aspartic acid bromomethyl ketone β-tert-butyl ester and 2,6-dichloro-3-N-motpholinyl sulfonamido)benzoic acid.

EXAMPLE 18
N-Methoxycarbonyl-L-Alanine-L-Aspartic Acid 2,6-dichloro-benzoyloxymethyl Ketone β-tert-Butyl Ester and other Compounds of Formula E Part A: N-benzyloxycarbonyl-L-aspartic acid 2,6-dichlorobenzoyloxymethyl ketone β-tert-butyl ester (1.02 g, 2 mmol) was dissolved in absolute ethanol (100 ml) containing 6 N aqueous HCl (0.67 ml, 4 mmol). 10% Palladium on carbon (96 mg) was added and the reaction mixture was stirred under an ambient atmosphere of hydrogen gas for approximately 1 hour (thin layer chromotography [5% MeOH—$CH_2Cl_2$] indicated the disappearance of starting material). The solution was filtered and the solvent was removed in vacuo to give L-aspartic acid 2,6-dichlorobenzoyloxymethyl ketone β-tert butyl ester-HCl salt (Formula D) which was used immediately in the subsequent reaction described in Part B.

Part B: A solution of N-methoxycarbonyl-L-alanine (301 mg, 2.05 mmol) in $CH_2Cl_2$ (10 ml) was cooled to −20° C. and isobutylchloroformate (0.28 ml, 2.05 mmol) and N-methylmorpholine (0.23 ml, 2.05 mmol) were added sequentially. The reaction mixture was stirred for 15 minutes and a solution of aspartic acid 2,6-dichlorobenzoyl methyl ketone β-tert-butyl ester-HCl salt (prepared in Part A above) followed by a second addition of N-methyl morpholine (0.23 ml, 2.05 mmol).

The reaction mixture was stirred for 30 minutes and was then diluted with EtOAc, washed with water, aqueous saturated $NaHCO_3$, brine and dried ($MgSO_4$). The solvents were removed in vacuo and the product purified by silica gel chromatography using 40% EtOAc-hexane as eluent to give N-methoxycarbonyl-L-alanine-L-aspartic acid 2,6-dichlorobenzoyl methyl ketone β-tert ester (0.72 g; 80%).

In a similarfashion the following compounds of Formula E were prepared:

EXAMPLE 19
N-2-Thienyl)carbonyl-L-aspartic acid 2,6-dichlorobenzoyloxy-methyl ketone β-tert-butyl ester from N-benzyloxycarbonyl-L-aspartic acid 2,6-dichlorobenzoyloxymethyl ketone β-tert-butyl ester and 2-thiophene carboxylic acid.

EXAMPLE 20
N-Methoxycarbonyl glycine-L-aspartic acid 2,6-dichlorobenzoyloxy-methyl ketone β-tert-butyl ester from N-benzyloxycarbonyl-L-aspartic acid 2,6-dichlorobenzoyloxymethyl ketone β-tert-butyl ester and N-methoxycarbonyl glycine.

EXAMPLE 21
N-Methoxycarbonyl-L-phenylalanine-L-aspartic acid 2,6-dichlorobenzoyloxymethyl ketone β-tert-butyl ester from N-benzyloxycarbonyl-L-aspartic acid 2,6-dichlorobenzoyloxymethyl ketone β-tert-butyl ester and N-methoxycarbonyl-L-phenyl alanine.

EXAMPLE 22
N-Methoxycarbonyl L-β-(2-thienyl)alanine-L-aspartic acid 2,6-dichlorobenzoyloxymethyl ketone β-tert-butyl ester from N-benzyloxycarbonyl-L-aspartic acid 2,6-dichlorobenzoyloxymethyl ketone β-tert-butyl ester and N-methoxycarbonyl-L-β-(2-thienyl)alaine.

EXAMPLE 23
N-Methoxycarbonyl-L-valine-L-aspartic acid 2,6-dichlorobenzoyl-oxymethyl ketone β-tert-butyl ester from N-benzyloxycarbonyl-L-aspartic acid 2,6-dichlorobenzoyloxymethyl ketone β-tert-butyl ester and N-methoxycarbonyl-L-valine.

EXAMPLE 24
N-Methoxycarbonyl-L-histidine-L-aspartic acid 2,6-dichloro-benzoyloxymethyl ketone β-tert-butyl ester from N-benzyloxy-carbonyl-L-aspartic acid 2,6-dichlorobenzoyloxymethyl ketone β-tert-butyl ester and N-methoxycarbonyl-L-histidine.

EXAMPLE 25

N-Benzyloxycarbonyl-L-alanine-L-aspartic acid 2,6-dichlorobenzoyloxymethyl ketone β-tert-butyl ester from N-benzyloxy-carbonyl-L-aspartic acid 2,6-dichlorobenzoyloxymethyl ketone β-tert-butyl ester and N-benzyloxycarbonyl-L-valine.

EXAMPLE 26

N-Benzyloxycarbonyl-L-alanine-L-aspartic acid 2,6-dichlorobenzoyloxymethyl ketone β-tert-butyl ester from N-benzyloxy-carbonyl-L-aspartic acid 2,6-dichlorobenzoyloxymethyl ketone β-tert-butyl ester and N-benzyloxycarbonyl-L-alanine.

EXAMPLE 27 i) Benzyloxycarbonyl-L-valine-L-alanine-L-aspartic acid 2,6-dichlorobenzoyloxymethyl ketone β-tert-butyl ester from N-benzyloxycarbonyl-L-aspartic acid 2,6-dichlorobenzoyloxymethyl ketone β-tert-butyl ester and N-benzyloxycarbonyl-L-valine-L-alanine.

EXAMPLE 28

N-2-Furoyl-L-Aspartic Acid 2,6-Dichlorobenzoyloxymethyl Ketone β-tert-Butyl Ester Part A: N-Benzyloxycarbonyl-L-aspartic acid 2,6-dichlorobenzoyloxymethyl ketone β-tert-butyl ester (1.02 g, 2 mmol) was dissolved in absolute ethanol (100 ml) containing 6 N aqueous HCl (0.67 ml, 4 mmol). 10% Palladium on carbon (96 mg) was added and the reaction mixture was stirred under an ambient atmosphere of hydrogen gas for approximately 1 hour (thin layer chromatography [15% MeOH—$CH_2Cl_2$] indicated the disappearance of starting material). The solution was filtered and the solvent was removed in vacuo to give L-aspartic acid 2,6-dichlorobenzoyloxymethyl ketone β-tert-ester-HCl salt (Formula D) which was used immediately in the subsequent reaction described in Part B.

Part B: To a solution of L-aspartic acid 2,6-dichlorobenzoyloxymethyl ketone β-tert-butyl ester-HCl salt (2.0 mmol, prepared in Part A above) in $CH_2Cl_2$ (10 ml) at 0° C. was added 2-furoyl chloride (0.21 ml, 2.05 mmol). N-methylmorpholine (0.25 ml; 2.10 mmol) was then added and the reaction mixture stirred for 1 hour as it slowly was allowed to warm to room temperature. The solution was diluted with EtOAc, washed with water, saturated aqueous $NaHCO_3$, brine and dried ($MgSO_4$). The solvents were removed in vacuo. The product was purified by silica gel chromatography using 30% EtOAc-hexane as eluent to give N-2-furoyl-L-aspartic acid 2,6-dichlorobenzoyloxymethyl ketone β-tert-butyl ester (mp 73–74° C.).

In a similar fashion the following compounds of Formula E were prepared:

EXAMPLE 29

N-2-Furonylcarbonyl-L-aspartic acid 2,6-dichloro-3-(N-morpholinylsulfonamido) benzoyloxymethyl ketone βtert-butyl ester from N-benzyloxycarbonyl-L-aspartic acid 2,6dichloro-3-(N-morpholinylsulfonamido) benzoyloxymethyl ketone β-tert-butyl ester and 2-furoic acid chloride.

EXAMPLE 30

N-(3-Phenylpropionyl)-L-aspartic acid 2,6-dichlorobenzoyloxy-methyl ketone β-tert-butyl ester from N-benzyloxycarbonyl-L-aspartic acid 2,6-dichlorobenzoyloxymethyl ketone β-tert-butyl ester and 3-phenylpropionyl chloride.

EXAMPLE 31

N-Methoxycarbonyl-L-aspartic acid 2,6-dichlorobenzoyloxymethyl ketone β-tert-butyl ester from N-benzyloxycarbonyl-L-aspartic acid 2,6-dichlorobenzoyloxymethyl ketone β-tert-butyl ester and methyl chloroformate.

EXAMPLE 32

N-(N,N-4-Dimethylaminomethyl)benzoyl-L-aspartic acid 2,6-dichlorobenzoyloxymethyl ketone β-tert-butyl ester (m.p. 63–65° C.) from 2,6-dichlorobenzoyloxymethyl ketone β-tert-butyl ester and 4-(N,N-dimethylaminomethyl) benzoyl chloride.

EXAMPLE 33

3-(N-Butylsulfonamidoyl)-2,6-dichlorobenzoic acid and Other Compound of Formula 3

Part A: Under an atmosphere of nitrogen gas, a reaction vessel was charged with 2,6-dichlorobenzoic acid (10 g, 53.55 mmol) (Formula F) and chlorosulfonic acid (3 ml, 472 mmol). The reaction mixture was refluxed for 1 hour and cooled to 10° C. The contents of the reaction vessel were poured slowly into 3 L of ice water. The white solid which precipitated was collected by filtration and dried in vacuo (10 mm) at 35° C. for 48 hours to give 3-(chlorosulfonyl)-2,6-dichlorobenzoic acid (Formula G) (9.2 g, 61% yield).

Part B: 3-(Chlorosulfonyl)-2,6-dichlorobenzoic acid (1.5 g; 5.2 mmol) was dissolved in anhydrous toluene (35 ml) to which was added powdered $K_2CO_3$ (1.44 g: 10.4 mmol) and n-butylamine (1.0 ml, 10.4 mmol). The reaction mixture was stirred at 25° C. for 12 hours. The solution was diluted slowly with 1 M ethereal HCl (20 ml) and was then stirred for 30 minutes. The solution was filtered and the resulting filtrate was evaporated to dryness to give crude product. Further purification of the material by silica gel chromatography using EtOAc as the eluent provided 3-N-butylsulfonamidoyl)-2,6-dichlorobenzoic acid (Formula 3) (1.43 g, 85%. $^1$H NMR (DMSO) d 8.11 (t, 1H), 7.98 and 7.71 (doublets, 1H each), 2.75 (m, 2H), 1.55 (m, 2H), 1.32 (m 2H), 0.87 (t, 3H)

In a similar manner, the following compounds were prepared:

EXAMPLE 34

2,6-Dichloro-3-sulfonamidoylbenzoic acid ($^1$H NMR (DMSO) d 8.11 (t, 1H), 7.42 and 7.15 (doublets, 1H each), 7.26 (d, 2H) from 3-chlorosulfonyl-2,6-dichlorobenzoic acid and 40% aqueous ammonium hydroxide.

EXAMPLE 35

3-(N-Benzylsulfonamidoyl)-2,6-dichlorobenzoic acid ($^1$H NMR (DMSO) d 8.70 (t, 1H), 7.90 and 7.65 (doublets, 1H each), 7.25 (m, 5H), 4.15 (m, 2H) from 3-chlorosulfonyl-2, 6-dichlorobenzoic acid and benzyl amine.

EXAMPLE 36

3-(N-[2-Aminoacetamido]sulfonamidoly)-2,6-dichlorobenzoic acid from 3-chlorosulfonyl-2,6-dichlorobenzoic acid and glycinamide (m.p. 210–213° C.

EXAMPLE 37

3-(N-Morpholino)sulfonamidoyl)-2,6-dichlorobenzoic acid from 3-chlorosulfonyl-2,6-dichlorobenzoic acid and morpholine.

EXAMPLE 38

N-Benzyloxycarbonyl-L-Aspartic Acid 2,6-Dichlorobenzoyloxymethyl Ketone and Other Compounds of Formula I A solution of β-tert-butyl ester of N-benzyloxycarbonyl-L-aspartic acid 2,6-dichlorobenzoyloxymethyl ketone (Example 2) in methylene chloride containing 25% v/v trifluoroacetic acid (20 ml) was stirred for 2 hours at 0° C. The solvent was removed in vacuo and the residue azeotroped time times with methylene chloride to give analytically pure N-benzyloxycarbonyl-L-aspartic acid 2,6-dichlorobenzoyloxymethyl ketone (high resolution mass spectrum for $C_{20}H_{17}Cl_2NO_7$ found 453.1572).

In a similar fashion, the following compounds of Formulas 1 and 2 were prepared:

EXAMPLE 39

N-Benzyloxycarbonyl-L-aspartic acid 2,6-difluorophenoxymethyl ketone (high resolution mass spectrum for $C_{19}H_{17}F_2NO_6$ found 393.3562) from the β-tert-butyl ester of Example 3.

EXAMPLE 40

N-Benzyloxycarbonyl-L-aspartic acid 2,6-ditrifluoromethyl benzoyloxymethyl ketone (high resolution mass spectrum for $C_{22}H_{17}O_7F_6$ found 521.1452) from the β-tert-butyl ester of Example 4.

EXAMPLE 41

N-Benzyloxycarbonyl-L-aspartic acid 2,6-dichlorophenoxymethyl ketone (mass spectrum m/z 426 (M+H) from the β-tert-butyl ester of Example 5.

EXAMPLE 42

N-Benzyloxycarbonyl-L-aspartic acid 2-fluoro-4-(N-morpholinyl sulfonamido)-phenoxymethyl ketone (m.p. 65–66° C.) from the β-tert-butyl ester of Example 6.

EXAMPLE 43

N-Benzyloxycarbonyl-L-aspartic acid 2-chloro-4-thiomorpholinylsulfonamido)-phenoxymethyl ketone (m.p. 180–181° C.) from the β-tert-butyl ester of Example 7.

EXAMPLE 44

N-Benzyloxycarbonyl-L-aspartic acid 2,6-dichloro-3-(2-N-morpholinylethoxy)-benzoyloxymethyl ketone (high resolution mass spectrum for $C_{26}H_{29}O_9N_2Cl_2$ found 583.1245) from the β-tert-butyl ester of Example 8.

EXAMPLE 45

N-Benzyloxycarbonyl-L-aspartic acid 2,6-dimethoxybenzoyloxy methyl ketone (high resolution mass spectrum for $C_{22}H_{24}O_9N$ found 446.1430) from the β-tert-butyl ester of Example 9.

EXAMPLE 46

N-Benzyloxycarbonyl-L-aspartic acid 2,6-dichloro-3-(benzyloxy) benzoyloxymethyl ketone (high resolution mass spectrum for $C_{27}H_{24}O_8NCl_2$ found 560.0865) from the β-tert-butyl ester of Example 10.

EXAMPLE 47

N-Benzyloxycarbonyl-L-aspartic acid 2-acetamido-6-chloro-benzoyloxymethyl ketone (high resolution mass spectrum for $C_{22}H_{22}O_8N_2Cl_2$ found 477.1044) from the β-tert-butyl ester of Example 11.

EXAMPLE 48

N-Benzyloxycarbonyl-L-aspartic acid 2,6-difluorobenzoyloxymethyl ketone (high resolution mass spectrum for $C_{20}H_{18}O_7NF_2$ found 422.1046) from the β-tert-butyl ester of Example 12.

EXAMPLE 49

N-Benzyloxycarbonyl-L-aspartic acid 3-(N-butylsulfonamido)-2,6-dichlorobenzoyloxymethyl ketone (m p. 48–50° C.) from the β-tert-butyl ester of Example 13.

EXAMPLE 50

N-Benzyloxycarbonyl-L-aspartic acid 2,6-dichloro-3-sulfonamidobenzoyloxymethyl ketone (m.p. 44–46° C.) from the β-tert-butyl ester of Example 14.

EXAMPLE 51

N-Benzyloxycarbonyl-L-aspartic acid 3-(N-benzylsulfonamido)-2,6-dichlorobenzoyloxymethyl ketone (m.p. 66–68° C.) from the β-tert-butyl ester of Example 15.

EXAMPLE 52

N-Benzyloxycarbonyl-L-aspartic acid 3-(N-[2-aminoacetamidoyl] sulfonamido)-2,6-dichlorobenzoyloxymethyl ketone (m.p. 54–56° C.) from the β-tert-butyl ester of Example 16.

EXAMPLE 53

N-Benzyloxycarbonyl-L-aspartic acid 2,6-dichloro-3-(N-morpholinyl-sulfonamido)benzoyloxymethyl ketone (high resolution mass spectrum for $C_{24}H_{25}O_{10}N_2Cl_2$ found 603.0594) from the β-tert-butyl ester of Example 17.

EXAMPLE 54

N-Methoxycarbonyl-L-alanine-L-aspartic acid 2,6dichlorobenzoyloxy-methyl ketone (Anal. calc. for $C_{17}H_{18}O_8Cl_2N_2$: C, 45.45; H, 4.04; N, 6.24. Found: C. 45.20; H, 4.06; N, 5.98) from the β-tert-butyl ester of Example 18.

EXAMPLE 55

N-(2-thienyl)carbonyl-L-aspartic acid 2,6-dichlorobenzoyloxymethyl ketone (mass spectrum m/z 430 (M+)) from the β-tert-butyl ester of Example 19.

EXAMPLE 56

N-Methoxycarbonyl-glycine-L-aspartic acid 2,6-dichlorobenzoyloxy-methyl ketone (Anal. calc. for $C_{16}H_{16}O_8Cl_2N_2$: C, 44.16; H, 3.17; N, 6.44. Found. C, 44.24; H, 3.15; N, 6.12) from the β-tert-butyl ester of Example 20.

EXAMPLE 57

N-Methoxycarbonyl-L-phenylalanine-L-aspartic acid 2,6-dichlorobenzoyloxymethyl ketone (Anal. calc. for $C_{23}H_{22}O_8Cl_2N_2$: C, 52.59; H, 4.22; N, 5.33. Found: C, 52.98; H, 4.38; N, 5.21) from the β-tert-butyl ester of Example 21.

EXAMPLE 58

N-Methoxycarbonyl-L-β-(2-thienyl)alanine-L-aspartic acid 2,6-di-chlorobenzoyloxymethyl ketone (mass spectrum m/z 531 (M+)) from the β-tert-butyl ester of Example 22.

EXAMPLE 59

N-Methoxycarbonyl-L-valine-L-aspartic acid 2,6-dichlorobenzoyloxy-methyl ketone (mp. 119–120° C.) from the β-tert-butyl ester of Example 23.

EXAMPLE 60

N-Methoxycarbonyl-L-histidine-L-aspartic acid 2,6-dichlorobenzoyl-oxymethyl ketone (Anal. calc. for $C_{22}H_{21}O_{10}F_3Cl_2N_4$: C, 41.99; H, 3.36; N, 8.90. Found: C, 42.08; H, 3.48; N, 8.67; mass spectrum m/z 515 (M+)) from the β-tert-butyl ester of Example 24.

EXAMPLE 61
N-Benzyloxycarbonyl-L-valine-L-aspartic acid 2,6-dichlorobenzoyloxy-methyl ketone (Anal. calc. for $C_{25}H_{26}O_8Cl_2N_2$: C, 54.26; H, 4.47; N, 5.06. Found: C, 54.06; H, 4.74; N, 4.91) from the β-tert-butyl ester of Example 25.

EXAMPLE 62
N-Benzyloxycarbonyl-L-alanine-L-aspartic acid 2,6-dichlorobenzoyl-oxymethyl ketone (mass spectrum m/z 525 (M+)) from the β-tert-butyl ester of Example 26.

EXAMPLE 63
N-Benzyloxycarbonyl-L-valine-L-alanine-L-aspartic acid 2,6-di-chlorobenzoyloxymethyl ketone (Anal. calc. for $C_{28}H_{31}O_9Cl_2N_3$: C, 53.85; H, 5.00; N, 6.73. Found: C, 54.00; H, 5.04; N, 6.66) from the β-tert-butyl ester of Example 27.

EXAMPLE 64
N-(2-Furonyl)carbonyl-L-aspartic acid 2,6-dichlorobenzoyloxymethyl ketone (mass spectrum m/z 414 (M+)) from the β-tert-butyl ester of Example 28.

EXAMPLE 65
N-(2-Furonyl)carbonyl-L-aspartic acid 2,6-dichloro-3-(N-morpholinylsulfonamido)benzoyloxymethyl ketone (mass spectrum m/z 563 (M+)) from the β-tert-butyl ester of Example 29.

EXAMPLE 66
N-(3-Phenylpropionyl)-L-aspartic acid 2,6-dichlorobenzoyloxymethyl ketone ($^1$H NMR (CDCl$_3$) d 7.40 (m, 9H), 5.05 (2xdd, 4H), 4,70 (m, 1H), 2.85 (m, 2H), 2.65 (dd, 1H), 2.60 (dd, 1H), 2.50 (m,2H) from the β-tert-butyl ester of Example 30.

EXAMPLE 67
N-Methoxycarbonyl-L-aspartic acid 2,6-dichlorobenzoyloxymethyl ketone ($^1$H NMR (DMSO) d 7.60 (m, 6H), 5.24 (m, 4H), 4.51 (m, 1H), 3.58 (s, 3H), 2.75 (dd, 1H), 2.55 (dd, 1H) from the β-tert-butyl ester of Example 31.

EXAMPLE 68
N-(4-N,N-dimethylaminomethyl)benzoyl-L-aspartic acid 2,6dichlorobenzoyloxymethyl ketone (m.p. 55–57° C.) from the β-tert-butyl ester of Example 32.

EXAMPLE 69
N-Benzyloxycarbonyl-D-aspartic acid 2,6-dichlorobenzoyloxymethyl ketone (high resolution mass spectrum for $C_{20}H_{17}C_{12}NO_7$, found 453.1583) from N-benzyloxycarbonyl-D-aspartic acid-β-tert-butyl ester and 2,6-dichlorobenzoic acid using the procedures described in Examples 1, 2 and 38.

EXAMPLE 70
N-(2-[2,6-dichlorobenzoyloxy])acetyl-L-aspartic acid 2,6-dichlorobenzoyloxymethyl ketone (mass spectrum m/z 551 (M$^+$) from N-Benzyloxycarbonyl-L-aspartic acid 2,6-dichlorobenzyloxymethyl ketone and 2-(2,6-dichlorobenzyloxy)acetic acid using the procedures described in Examples 18 and 38.

EXAMPLE 71
N-Benzyloxycarbonyl-L-valine-L-aspartic acid 4-(N,N-diethyl-sulfonamido)-2,3,5,6-tetrafluorophenoxymethyl ketone (mass spectrum m/z 664 (M+H) from N-Benzyloxycarbonyl-L-aspartic acid bromomethyl ketone β-tert-butyl ester, N-benzyloxycarbonyl-L-valine and 4-(N, N-diethylsulfonamido)-2,3,5,6-tetrafluorophenol using the procedures described in Examples 2, 18 and 38. The 4-(N, N-diethyl-2,3,5,6-tetrafluorophenol was prepared by reacting 2,3,5,6-tetrafluorophenol with chlorosulfonic acid followed by reaction with diethylamine, analogous to the procedure described in Scheme III, and Example 33.

Compounds of the present invention were tested for IL-1β protease inhiβition activity according to the following protocol:

Partially purified IL-1β protease is stored at −80° C., thawed on ice, and preincuβated for 10 minutes at 37° C. with 2.5 mM dithiothreitol in a buffer solution containing 10 mM Tris-HCl (pH 8.0) and 25% (v/w) glycerol. Inhibitors are prepared as stock solutions in dimethyl sulfoxide (DMSO). The protease is preincubated with inhibitor in a volume of 20 ml in a 1.5 ml polypropylene microcentrifuge tube for 15 minutes at 37° C. The volume of compound added to the assay is adjusted to yield a DMSO concentration in the preincubation of <15% (v/v). The enzyme assay is then initiated by the addition of substrate (TRITC-AYVHDAPVRS-NH$_2$) to yield a final concentration of 67 mM in a final volume of 30 mL. The reaction are carried out for 60 minutes at 37° C. in the dark and are terminated by the addition of 10 ml of 10% trifluoroacetic acid (TFA). Following the addition of 115 ml of 0.1% TFA, the samples are analyzed by high pressure liquid chromatography using a reverse phase (C18) column and elution with an acetonitrile/water/TFA gradient. Substrate and product are monitored by their absorbance at 550 nm and elute at 4.2 and 5.2 minutes, respectively.

TABLE I

| Example No. | Name of Compound | IC$_{50}$ μm |
|---|---|---|
| 38 | N-Benzyloxycarbonyl-L-aspartic acid 2,6-dichlorobenzoyloxymethyl ketone | 0.05 |
| 40 | N-Benzyloxycarbonyl-L-aspartic acid 2,6-ditrifluoromethylbenzoyloxymethyl ketone | 0.10 |
| 41 | N-Benzyloxycarbonyl-L-aspartic acid 2,6-dichlorophenoxymethyl ketone | 0.10 |
| 42 | N-Benzyloxycarbonyl-L-aspartic acid 2 fluoro-4-(N-morpholinyl sulfonamido)phenoxymethyl ketone | 0.32 |
| 49 | N-Benzyloxycarbonyl-L-aspartic acid 3-(N-butylsulfonamido)-2,6-dichlorobenzoyloxymethyl ketone | 0.09 |
| 52 | N-Benzyloxycarbonyl-L-aspartic acid 3-(N-[2-aminoacetamidoyl]sulfonamido)-2,6-dichlorobenzoyloxymethyl ketone | 0.06 |
| 53 | N-Benzyloxycarbonyl-L-aspartic acid 2,6-dichloro-3-(N-morpholinylsulfonamido)-benzoyloxymethyl ketone | 0.09 |
| 54 | N-Methoxycarbonyl-L-alanine-L-aspartic acid 2,6-dichlorobenzoyloxymethyl ketone | 0.06 |
| 57 | N-Methoxycarbonyl-L-phenylalanine-L-aspartic acid 2,6-dichlorobenzoyloxymethyl ketone | 0.07 |
| 64 | N-(2-furonyl)carbonyl-L-aspartic acid 2,6-dichlorobenzoyloxymethyl ketone | 0.14 |
| 67 | N-Methoxycarbonyl-L-aspartic acid 2,6-dichlorobenzoyloxymethyl ketone | 0.08 |
| 68 | N-(4-(N,N-dimethylaminomethyl)benzoyl-L-aspartic acid 2,6-dichlorobenzoyloxymethyl ketone | 0.3 |
| 70 | N-(2-[2,6-dichlorobenzoyloxy])acetyl-L-aspartic acid 2,6- dichlorobenzoyloxymethyl ketone | 0.2 |

Compounds of the present invention were tested for their ability to block mature IL-1β release from cells (monocytes) as described in the following protocol:

PROTOCOL FOR MONITORING RELEASE OF MATURE IL-1β-FROM HUMAN MONOCYTES

Human monocytes were isolated from heparinized leukopheresis units obtained through Biological Specialty Corporation (Lansdale, Pa.). Monocytes were purified by Ficoll-Hupaque (Pharnacia Fine Chemicals, Piscataway, N.J.) gradient centrifugation and more than 95% pure monocyte populations obtained by centrifugal elutriation. The assay was performed on duplicate samples of freshly isolated human monocytes, cultured in suspension at 37° C. and rotated gently in conical bottom polypropylene tubes (Sardstedt Inc., Princeton, N.J.). Human monocytes at a concentration of $5 \times 10^6$ cells/mL were resuspended in 1 mL of RPMI 1640 (a common tissue buffer from M.A. Bioproducts, Walkersville, Md.) containing 1% fetal calf serum (FCS) (HyClone, Logan, Utah) and 50 μg/mL gentamycin (Gibco, Grand Island, N.Y.). The cells were treated either with a compound of the invention (i.e. test compound) or with a non-inhibitor (control compound, typically 0.03% DMSO) for 15 minutes and then activated with 0.01% fixed Staphylococcus aureus (The Enzyme Center, Malden, Mass.) for 1 hour. The cells were then centrifuged and resuspended in 1 mL of cysteine, methionine-free RPMI media containing 1% dialyzed FCS (Hyclone). The cells were pretreated with a test compound or control compound for 15 minutes after which 0.01% fixed S. aureus plus 100 μCi Tran 35-S label (ICN, Ivine, Calif.) was added and the cells incubated at 37° C. for 1 hour. After incubation, cells were centrifuged, washed once in phosphate buffer saline and resuspended in 1 mL RPMI containing 1% fetal calf serum The cells were again pretreated with a test or control compound for 15 minutes and then 0.01% S. aureus for 2 hours. At the end of the incubation, cells were centrifuged and supernates saved for immunoprecipitation. Cells were washed once in phosphate buffer saline and then lysed in RIPA, a continuous cell media buffer containing 2 mM phenylmethylsulfonyl fluoride, 10 mM iodoacetate, 1 μg/mL pepstatin A, 1 μg/mL leupeptin and 0.5 TIU aprotinin.

For the immunoprecipitations, an equal volume of 1% dry milk in RIPA buffer plus 50 μL of resuspended protein A sepharose CL-4B (Pharmacia, Piscataway, N.Y.) was added to supernates and 1 mL of 4% dry milk containing protein A sepharose CL4B to cell lysates and samples rotated for 30 minutes at 4° C. Beads were then centrifuged down, samples transferred to fresh tubes and incubated overnight with 40 μg rabbit anti-human IL-1B polyclonal antibody (Genzyme, Cambridge, Mass.). The IL-1β proteins were then precipitated with 70 μL protein A sepharose, resuspended in 60 μL SDS sample buffer and run on 15% SGD-PAGE gels. Autoradiography was performed on dried gels and the amount of radioactivity (counts per minute, cpm) quantitated using a Betascope 603 analyzer.

Data Analysis

In the monocyte pulse chase assay, each test parameter was run in duplicate. Data was collected from the Beta Scope using a personal computer, then transferred to the VAX system for calculation of mean cpm and standard deviation of the mean. When test compounds were evaluated, the percent inhibition of release of mature IL-1β was calculated as follows:

100×[1−(cells treated with stimuli+test compound−unstimulated cells)/(cells treated with stimuli+control compound−unstimulated cells)]

These % inhibition values were then used to calculate $IC_{50}$ value for each compound. Since the human monocyte pulse chase assay uses primary cells from different donors, each test compound was run in 2–3 separate experiments, using monocytes from 2–3 different donors.

| Results | |
| --- | --- |
| Example | in vivo $IC_{50}$ (μM) |
| 38 | 10 |
| 45 | ca. 100 |
| 48 | ca. 100 |
| 59 | 10 |
| 61 | 0.9 |
| 63 | 0.5 |
| 65 | 30 |
| 69 | 10 |
| 71 | 5 |

---

What is claimed is:

1. A compound of the formula (I)

Formula I

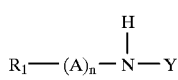

wherein:
n is 0–3;
Y is

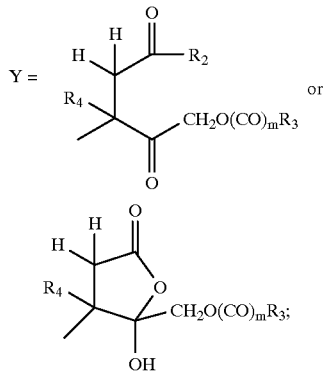

m is 1;
$R_3$ is a singularly or multiply substituted phenyl ring, wherein the substituents are:
H,
halogen,
OH,
$CF_3$,
$NO_2$,
$OR_5$,
$COR_9$,
$NR_6COR_{10}$,
$CONR_5R_6$,
$SO_2NR_5R_6$,
$SO_2R_6$,
$COOR_{11}$,
lower alkyl, or
lower cycloalkyl;
$R_5$ is lower straight or branched chain alkyl, lower cycloalkyl, —$(CR_6R_7)_{0-6}$-aryl or —$(CR_6R_7)_{0-6}$-heteroaryl;
$R_6$ and $R_7$ are independently H, lower straight chain or branched alkyl, benzyl, or cycloalkyl;
$R_9$ is lower straight or branched chain alkyl or lower cycloalkyl;
$R_{10}$ is $R_9$, $OR_{11}$, or $NR_6R_{11}$, wherein:
$R_{11}$ is lower straight or branched chain alkyl or lower cycloalkyl;

$R_4$ is H or deuterium;
$R_2$ is $OR_6$, $NR_6OR_7$, or $NR_6R_7$;
A is alanine, phenylalanine or valine;
$R_1$ is an acyl group of the formula (III):

Formula III

wherein:
$R_{12}$ is
$OR_5$,
$NR_5R_6$,
$R_5$,
—CH=CHR_5$,

[structures]

wherein
$R_{15}$ is a single bond, $(CH_2)_2$—6—$NR_6$—, or $(CH_2)_{2-6}$—O—; provided that $R_{12}$ is not $R_5$, wherein $R_5$ is phenylethyl.

2. A compound according to claim 1 selected from the group consisting of: N-Benzyloxycarbonyl-L-aspartic acid 2,6-difluorobenzoyloxy-methyl ketone, N-Benzyloxycarbonyl-L-aspartic acid 3-(N-butylsulfonamido)-2,6-dichlorobenzoyloxymethyl ketone, N-Benzyloxycarbonyl-L-aspartic acid 2,6-dichloro-3-sulfonamido benzoylmethyl ketone, N-Benzyloxycarbonyl-L-aspartic acid 3-(N-benzylsulfonamido)-2,6-dichlorobenzoyloxymethyl ketone and N-Benzyloxycarbonyl-L-aspartic acid 3-(N-[2-aminoacetamidoyl] sulfonamido)-2,6-dichlorobenzoyloxymethyl ketone.

3. A compound according to claim 1 selected from the group consisting of: N-Benzyloxycarbonyl-L-aspartic acid 2,6-dichloro-3-(N-morpholinylsulfonamido) benzoyloxymethyl ketone, N-Methoxycarbonyl-L-alanine-L-aspartic acid 2,6-dichlorobenzoyloxy-methyl ketone, N-(2-thienyl) carbonyl-L-aspartic acid 2,6-dichlorobenzoyloxy-methyl ketone, N-Methoxycarbonyl-glycine-L-aspartic acid 2,6-dichlorobenzoyloxymethyl ketone and N-Methoxycarbonyl-L-phenylalanine-L-aspartic acid 2,6-dichloro-benzoyloxymethyl ketone.

4. A compound selected from the group consisting of: N-Benzyloxycarbonyl-L-aspartic acid 2,6-dichlorobenzoyloxy-methyl ketone, N-Benzyloxycarbonyl-L-aspartic acid 2,6-difluorophenoxymethyl ketone, N-Benzyloxycarbonyl-L-aspartic acid 2,6-(ditrifluoromethyl)benzoyloxymethyl ketone, N-Benzyloxycarbonyl-L-aspartic acid 2,6-dichlorophenoxymethyl ketone, N-Benzyloxycarbonyl-L-aspartic acid 2-fluoro-4-(N-morpholinylsulfonamido) phenoxymethyl ketone, N-Benzyloxycarbonyl-L-aspartic acid 2-chloro-4-(N-thiomorpholinylsulfonamido) phenoxymethyl ketone, N-Benzyloxycarbonyl-L-aspartic acid 2,6-dichloro-3-(2-N-morpholinylethoxy) benzyloxymethyl ketone, N-Benzyloxycarbonyl-L-aspartic acid 2,6-dimethoxybenzoyloxy methyl ketone, N-Benzyloxycarbonyl-L-aspartic acid 2,6-dichloro-3-(benzyloxy)benzyloxymethyl ketone, N-Benzyloxycarbonyl-L-aspartic acid 2-acetamido-6-chlorobenzoyloxymethyl ketone, N-Methoxycarbonyl-L-β-(2-thienyl)alanine-L-aspartic acid 2,6-dichlorobenzoyloxymethyl ketone, N-Methoxycarbonyl-L-valine-L-aspartic acid 2,6-dichlorobenzoyloxymethyl ketone, N-Methoxycarbonyl-L-histidine-L-aspartic acid 2,6-chlorobenzoyloxy-methyl ketone, N-Benzyloxycarbonyl-L-valine-L-aspartic acid 2,6-dichlorobenzoyloxymethyl ketone, N-Benzyloxycarbonyl-L-alanine-L-aspartic acid 2,6-dichlorobenzoyloxymethyl ketone, N-Benzyloxycarbonyl-L-valine-L-alanine-L-aspartic acid 2,6-dichlorobenzoyloxymethyl ketone, N-(2-furonyl)carbonyl-L-aspartic acid 2,6-dichlorobenzoyloxymethyl ketone, N-(2-furonyl)carbonyl-L-aspartic acid 2,6-dichloro-3-(N-morpholinylsulfonamido)-benzoyloxymethyl ketone, N-(3-phenylpropionyl)-L-aspartic acid 2,6-dichlorobenzoyloxymethyl ketone, N-Methoxycarbonyl-L-aspartic acid 2,6-dichlorobenzoyloxymethyl ketone, N-(4-(N,N-dimethylaminomethyl)benzoyl-L-aspartic acid 2,6-dichlorobenzoyloxymethyl ketone, N-benzyloxycarbonyl-D-aspartic acid 2,6-dichlorobenzoyloxymethyl ketone, N-(2-[2,6-dichlorobenzoyloxy])acetyl-L-aspartic acid 2,6-dichlorobenzoyloxymethyl ketone and N-Benzyloxycarbonyl-L-valine-L-aspartic acid N-Benzyloxycarbonyl-L-valine-L-aspartic acid 4-(N,N-diethylsulfonamido)-2,3,5,6-tetrafluorophenoxymethyl ketone.

5. A pharmaceutical composition comprising:
a) a compound according to any one of claims 2, 3, or 4 in an amount effective for treating a disease or disorder selected from the group consisting of infectious disease, respiratory disease, inflammatory conditions, immune-based disease, auto-immune disease, bone disease, and tumors; and
b) a pharmaceutically acceptable carrier.

6. A pharmaceutical composition comprising:
a) a compound according to any one of claims 2, 3, or 4 in an amount effective for treating a disease or disorder selected from the group consisting of meningitis, salpingitis, septic shock, arthritis, rheumatoid arthritis, acute myelogenous leukemia, chronic myelogenous leukemia, cholangitis, colitis, encephalitis, endocerolitis, hepatitis, pancreatitis, reperfusion injury, hypersensitivity, and multiple sclerosis; and
b) a pharmaceutically acceptable carrier.

7. The pharmaceutical composition according to claim 6, wherein the disease or disorder is septic shock, rheumatoid arthritis, osteoarthritis, inflammatory bowel disease, or pancreatitis.

8. A pharmaceutical composition comprising:
a) a compound according to any one of claims 2, 3, or 4 in an amount effective for inhibiting interleukin-1β protease; and
b) a pharmaceutically acceptable carrier.

9. The pharmaceutical composition of claim 8 wherein said compound is selected from the group consisting of: N-Benzyloxycarbonyl-L-aspartic acid 2,6-difluorobenzoyloxymethyl ketone, N-Benzyloxycarbonyl-L-aspartic acid 3-(N-butylsulfonamido)-2,6-dichlorobenzoyloxymethyl ketone, N-Benzyloxycarbonyl-L-aspartic acid 2,6-dichloro-3-sulfonamido benzoylmethyl ketone, N-Benzyloxycarbonyl-L-aspartic acid 3-(N-benzylsulfonamido)-2,6-dichlorobenzoyloxymethyl ketone and N-Benzyloxycarbonyl-L-aspartic acid 3-(N-[2-aminoacetamidoyl] sulfonamido)2,6-dichlorobenzoyloxymethyl ketone.

10. The pharmaceutical composition of claim 8 wherein said compound is selected from the group consisting of: N-Benzyloxycarbonyl-L-aspartic acid 2,6-dichloro-3-(N-morpholinylsulfonamido) benzoyloxymethyl ketone, N-Methoxycarbonyl-L-alanine-L-aspartic acid 2,6-dichlorobenzoyloxy-methyl ketone, N-(2-thienyl) carbonyl-L-aspartic acid 2,6-dichlorobenzoyloxy-methyl ketone, N-Methoxycarbonyl-glycine-L-aspartic acid 2,6-dichlorobenzoyloxy-methyl ketone and N-Methoxycarbonyl-L-phenylalanine-L-aspartic acid 2,6-dichlorobenzoyloxymethyl ketone.

11. A pharmaceutical composition for inhibiting interleukin-1β protease comprising a compound selected from the group consisting of: N-Benzyloxycarbonyl-L-aspartic acid 2,6-dichlorobenzoyloxymethyl ketone, N-Benzyloxycarbonyl-L-aspartic acid 2,6-difluorophenoxymethyl ketone, N-Benzyloxycarbonyl-L-aspartic acid 2,6-ditrifluoromethyl benzoyloxymethyl ketone, N-Benzyloxycarbonyl-L-aspartic acid 2,6-dichlorophenoxymethyl ketone, N-Benzyloxycarbonyl-L-aspartic acid 2flouro-4-(N-morpholinylsulfonamido) phenoxymethyl ketone, N-Benzyloxycarbonyl-L-aspartic acid 2-chloro-4-(N-thiomorpholinylsulfonamido) phenoxymethyl ketone, N-Benzyloxycarbonyl-L-aspartic acid 2,6-dichloro-3-(2-N-morpholinylethoxy) benzyloxymethyl ketone, N-Benzyloxycarbonyl-L-aspartic acid 2,6-dimethoxybenzoyloxymethyl ketone, N-Benzyloxycarbonyl-L-aspartic acid 2,6-dichloro-3-(benzyloxy)-benzyloxymethyl ketone, N-Benzyloxycarbonyl-L-aspartic acid 2-acetamido-6-chlorobenzoyloxymethyl ketone, N-Methoxycarbonyl-L-b-(2-thienyl)alanine-L-aspartic acid 2,6-dichlorobenzoyloxymethyl ketone, N-Methoxycarbonyl-L-valine-L-aspartic acid 2,6-dichlorobenzoyloxymethyl ketone, N-Methoxycarbonyl-L-histidine-L-aspartic acid 2,6-dichlorobenzoyloxymethyl ketone, N-Benzyloxycarbonyl-L-valine-L-aspartic acid 2,6-dichlorobenzoyloxymethyl ketone, N-Benzyloxycarbonyl-L-alanine-L-aspartic acid 2,6-dichlorobenzoyloxymethyl ketone, N-Benzyloxycarbonyl-L-valine-L-alanine-L-aspartic acid 2,6-dichlorobenzoyloxymethyl ketone, N-(2-furonyl)carbonyl-L-aspartic acid 2,6- dichlorobenzoyloxymethyl ketone, N-(2-furonyl)carbonyl-L-aspartic acid 2,6-dichloro-3-(N-morpholinylsulfonamido)-benzoyloxymethyl ketone, N-(3-phenylpropionyl)-L-aspartic acid 2,6-dichlorobenzoyloxymethyl ketone, N-Methoxycarbonyl-L-aspartic acid 2,6-dichlorobenzoyloxymethyl ketone, N-(4-(N,N-dimethylaminomethyl)benzoyl-L-aspartic acid 2,6-dichlorobenzoyloxymethyl ketone, N-benzyloxycarbonyl-D-aspartic acid 2,6dichlorobenzoyloxymethyl ketone, N-(2-[2,6-dichlorobenzoyloxy])acetyl- L-aspartic acid 2,6-dichlorobenzoyloxymethyl ketone and N-Benzyloxycarbonyl-L-valine-L-aspartic acid 4-(N,N-diethylsulfonamido)-2,3,5,6-tetrafluorophenoxymethyl ketone.

\* \* \* \* \*

SEQUENCE LISTING (1) GENERAL INFORMATION:

(iii) NUMBER OF SEQUENCES:1

(2) INFORMATION FOR SEQ ID NO:1:

(i) SEQUENCE CHARACTERISTICS:
       (A) LENGTH:10 Amino Acids
       (B) TYPE:Amino Acid
       (C) STRANDEDNESS:
       (D) TOPOLOGY:Linear (ii) MOLECULE TYPE:Peptide (ix) FEATURE:
       (A) NAME/KEY: Modified-site
       (B) LOCATION: -1
       (D) OTHER INFORMATION: /label=TRITC
           /note="TRITC is tetramethylrhodamine isothiocyanate".

```
    (x) FEATURE:
        (A) NAME/KEY: Modified-site
        (B) LOCATION:  11
        (D) OTHER INFORMATION:

(xi) SEQUENCE DESCRIPTION: SEQ ID NO: 1:

Ala Tyr Val His Asp Ala Pro Val Arg Ser
    1               5                   10
```